United States Patent
Kirk

[11] Patent Number: 5,938,644
[45] Date of Patent: Aug. 17, 1999

[54] NEEDLE PROTECTION HOLDER

[75] Inventor: Kevin F. Kirk, Walled Lake, Mich.

[73] Assignee: Chrisom, Inc., Franklin, Mich.

[21] Appl. No.: 09/144,904

[22] Filed: Sep. 1, 1998

[51] Int. Cl.[6] ............................................ A61M 5/00
[52] U.S. Cl. .............................................. 604/263; 604/192
[58] Field of Search ............................... 604/263, 198, 604/192, 110, 195, 187

[56] References Cited

U.S. PATENT DOCUMENTS

| | | |
|---|---|---|
| 4,752,292 | 6/1988 | Lopez et al. . |
| 4,850,961 | 7/1989 | Wanderer et al. . |
| 4,850,977 | 7/1989 | Bayless ................................ 604/263 X |
| 4,927,416 | 5/1990 | Tomkiel . |
| 5,030,209 | 7/1991 | Wanderer et al. . |
| 5,106,379 | 4/1992 | Leap . |
| 5,135,510 | 8/1992 | Maszkiewicz et al. ............ 604/198 X |
| 5,147,326 | 9/1992 | Talonn et al. ..................... 604/263 X |
| 5,242,416 | 9/1993 | Hutson . |
| 5,346,480 | 9/1994 | Hess et al. . |
| 5,364,362 | 11/1994 | Schulz ................................ 604/192 X |
| 5,376,080 | 12/1994 | Petrussa . |
| 5,514,107 | 5/1996 | Haber et al. . |
| 5,562,624 | 10/1996 | Righi et al. . |
| 5,591,138 | 1/1997 | Vaillancourt ...................... 604/263 |
| 5,695,475 | 12/1997 | Best, Jr. et al. ................... 604/198 |
| 5,695,476 | 12/1997 | Harris . |

*Primary Examiner*—John D. Yasko
*Attorney, Agent, or Firm*—Dykema Gossett PLLC

[57] ABSTRACT

The needle protection holder is a device that encloses a syringe and needle within a tubular shell or cylinder after the needle has been used. Its intended purpose is to remove a needle attached to a syringe from a patient, both human and animal, thereby containing the needle safely within the cylinder. The device disallows the exchange of bodily fluids caused by needle sticks which are known to cause serious illness including death in medical technicians.

22 Claims, 4 Drawing Sheets

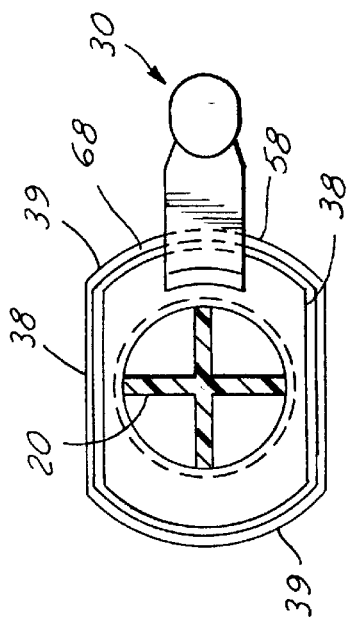
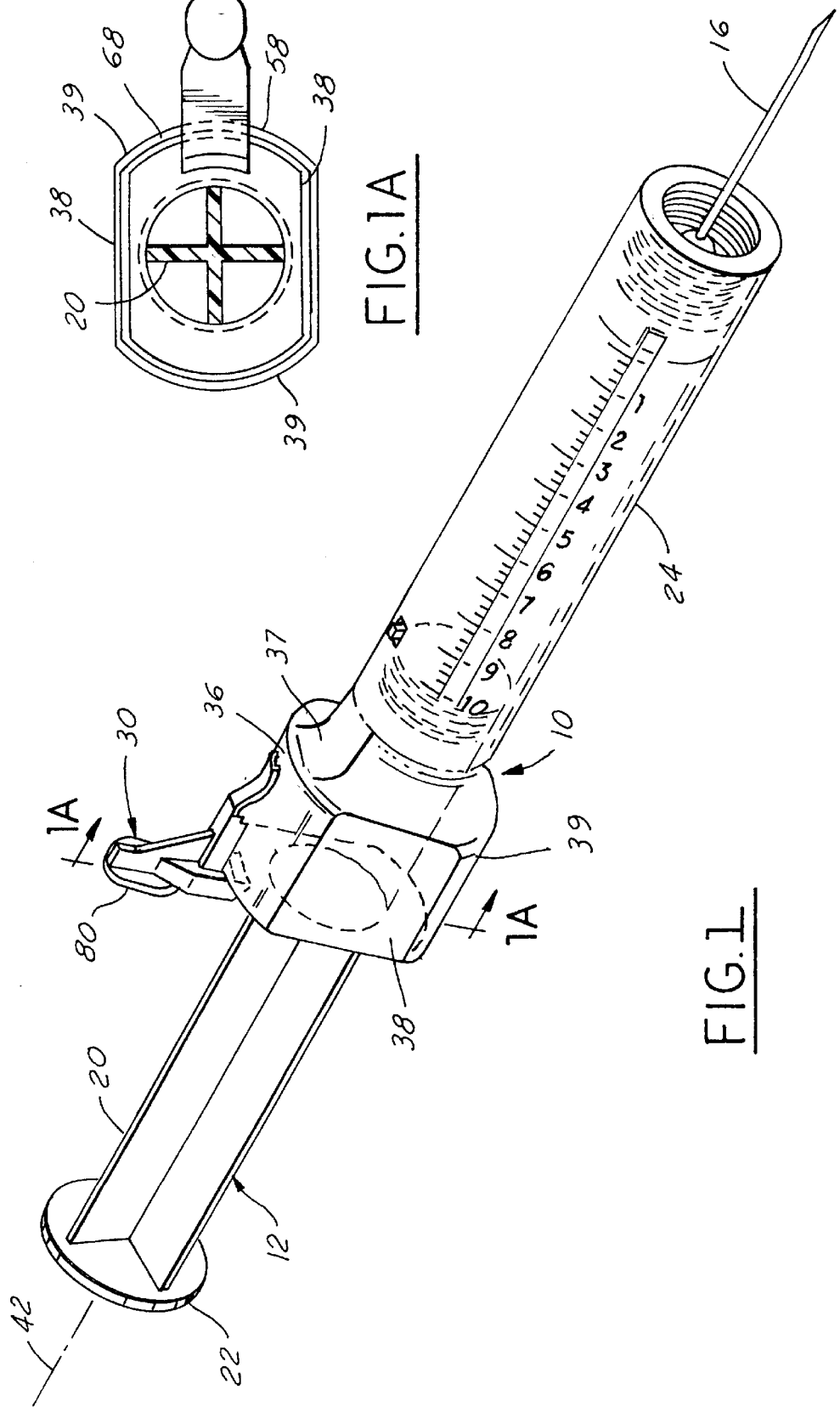

NEEDLE PROTECTION HOLDER

BACKGROUND OF THE INVENTION

1. Field of the Invention

The present invention relates generally to the art of syringes and more particularly to needle protection assemblies or shielding devices for syringes in order to reduce the likelihood of unintentional puncture of human beings and animals.

2. Description of the Prior Art

The spread of Acquired Immune Deficiency Syndrome or AIDS in the 1980's has greatly increased the concern of health care providers over the spread of communicable diseases through accidental needle pricks or punctures. Health care personnel including nurses, doctors and other providers accidentally prick themselves with needles on an average of two or more times a year. With the increase in AIDS, the chance of a health care provider being pricked by an AIDS contaminated needle over a period of years has become quite high and of great concern not only to health care personnel but also to government officials. In addition, other severe but less deadly diseases are known, such as hepatitis, which are transmitted through contaminated needle pricks or punctures. Such punctures occur in many ways, such as a nurse tripping while carrying a used and exposed needle or even while trying to cap a used needle.

Consequently, a greater need has developed for shielding devices or protection devices for needles of syringes such that the shielding devices are effective, easy to use and require only minor modifications to allow use with conventional types of syringes of the disposable and non-disposable types. Numerous devices have been developed to reduce the risk of accidental needle pricks.

Many of these devices include a cylindrical sheath secured to the syringe which may be telescopically advanced and retracted to enclose and expose the needle of the syringe. The currently available shielding devices that provide a cylindrical sheath to telescopically encircle the needle of a syringe suffer several deficiencies or shortcomings. Many of the existing devices require an operator such as a doctor, nurse or technician to use both hands to position the protection sheath in encircling relation with the syringe needle thereby increasing the likelihood of accidental needle pricks. Thus, when the user reaches with one hand to extend the sheath of the syringe, the medical attendant accidentally sticks the free hand through carelessness, being bumped or the like.

In many of the existing devices, the protective sheaths cannot be locked in encircling relationship with the syringe needle possibly resulting in accidental needle pricks if a compressed force is inadvertently applied to the protective sheath of the syringe. In other existing devices, the protective sheath permanently locks in protective relation with the syringe needle when advanced thereto preventing immediate protection of the syringe needle where the syringe must be used more than once for a given procedure. Existing sheathing devices also tend to require major modifications to existing syringes or greatly interfere with the normal use of the syringe.

SUMMARY OF THE INVENTION

It is a feature of the present invention to provide a novel needle protection holder or assembly for various types of syringes which minimizes the likelihood of accidental puncture.

Another feature of the present invention is to provide a needle protection holder for a syringe which, after utilization, isolates the used needle within the holder so as to render such needle harmless.

Still another feature of the present invention is to provide a needle protection holder or assembly for a syringe which is operable utilizing only one hand thereby permitting the other hand of the medical technician to be used for other purposes.

A still further feature of the present invention is to provide a needle protection holder or assembly for a syringe which includes a spring which is compressed during the injection of the fluid in the syringe into the patient whereafter the compressed spring is released which is effective to retract into the interior of the holder the needle to prevent its reuse.

Still another feather of the present invention is to provide a needle protection holder which is adaptable to various types of syringes including standard syringes and Luer Lok syringes, which is economical to manufacture and is efficient to use while preventing accidental punctures of humans and animals.

These as well as other features are accomplished by providing a device that encloses a syringe and needle within a tubular shell after the needle has been used. Its intended purpose is to remove the needle attached to a syringe from a patient, both human and animal, thereby containing the needle safely within its casing or housing. The needle protection holder disallows the exchange of bodily fluids caused by needle sticks or punctures. Such punctures can result in severe illness including death and such risk can be deterred by using the present invention.

A further feature of the present invention is that the needle protection holder or syringe retractor assembly can be manufactured in different sizes to fit virtually any Luer Lok or regular point syringe on the market. Thus, the present invention will permit hospitals and clinics to select any standard brand of syringe to use with the needle protection holder of the present invention. Thus, a medical institution can use the needle protection holder along with its own brands of standard syringes, thereby preserving the institution's ability to meet financial goals while providing employees with a safe environment and peace of mind knowing that accidental punctures have been greatly diminished or eliminated.

While the needle protection holder or syringe retractor of the present invention is intended for single usage, a medical technician could, if needed, unlock its mechanism and reuse the same syringe. This could prove useful in situations where multiple usage of a syringe is required such as in the administration of numbing or pain killing drugs to the same patient. This needle protection holder or device appears to be the first device to fit and lock onto a Luer Lok and onto a regular point syringe. A feature of the present invention is the provision of an attachment washer which is designed to connect a syringe and a needle utilizing the same method currently used to connect a syringe and a needle together. The Luer Lok and regular point syringe are two of the most common syringes currently used by hospitals and by veterinary clinics and would, therefore, provide a great deal of risk management protection. Thus, the needle protection holder or syringe retractor or device has been designed so that the medical technician can manipulate it with only one hand thereby freeing up the technicians other hand for other vital medical operations. It is well known that time can make the difference between life and death in many medical situations and can also effect the efficiency in which the medical technician cares for his or her own safety. With the present invention, virtually no time is lost in preparing the device for use; assembly takes only a matter of a few seconds to complete. Once the technician has administered the injection, the touch of the spring biased latch causes the needle to retract safely within the constraints of the tubular housing.

Other advantages and features of the present invention shall become apparent from the following detailed description of the preferred embodiment thereof, when taken in conjunction with the drawings wherein like reference characters refer to corresponding parts in the several views.

The drawings constitute a part of this specification and include an exemplary embodiment of the present invention and illustrate various features thereof.

BRIEF DESCRIPTION OF THE DRAWINGS

FIG. 1 is a perspective view of the syringe and the needle protection holder, with the syringe filled with a medication and the syringe plunger and the needle in extended positions ready for use.

FIG. 1A is a fragmentary sectional view taken on the line A—A of FIG. 1.

DETAILED DESCRIPTION OF A PREFERRED EMBODIMENT

Figure 2:
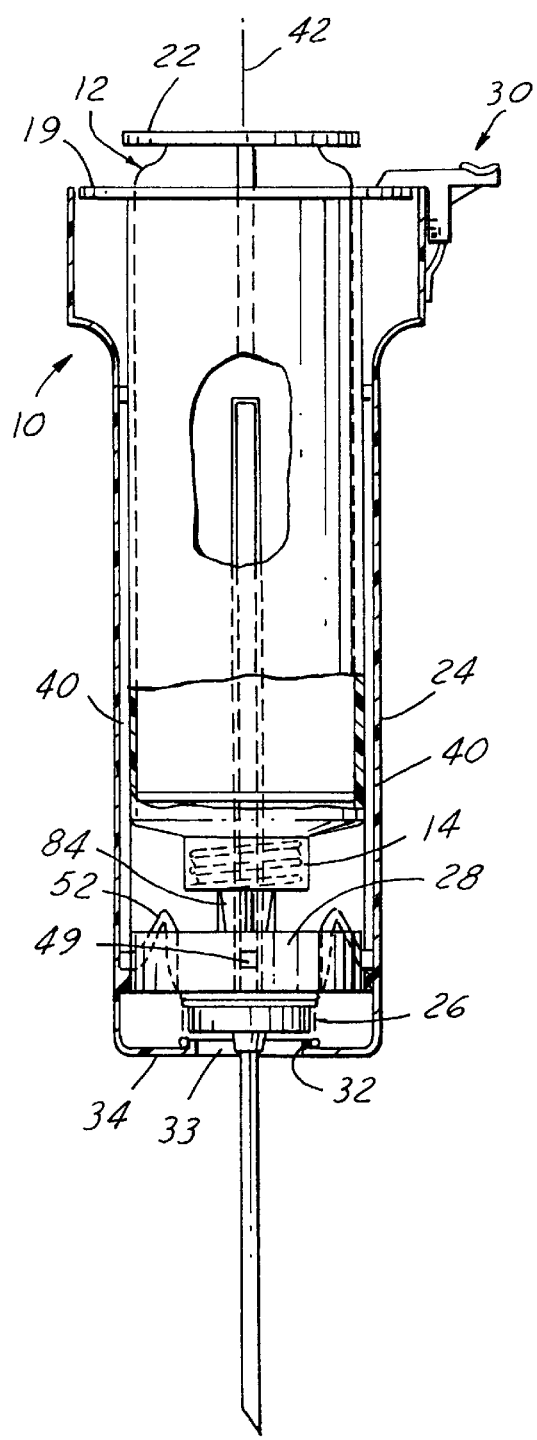
FIG. 2 is a side view of the needle protection holder and syringe with parts broken away and in section to expose the interior of the holder and syringe and showing the needle in an extended position after fluid has been applied to a patient.

The needle protection holder or syringe retractor 10 receives a conventional disposable or non-disposable hypodermic syringe 12 having a Luer Lok coupling 14 and a needle hub 15 at one end of a barrel 18. A plunger 20 with a finger flange 22 is received in the other end of the barrel 18. The barrel 18 at its opened end is provided with a flange 19. The outer surface of the barrel 18 is provided with suitable graduations to indicate the capacity of the medication to the administered.

The needle protection holder 10 consists of four main parts or components including the main housing tube or cylinder 24, a compression spring 26, an attachment washer or washer assembly 28 to which a removable needle 16 is connected and a thumb pedestal latch 30 affixed to the main cylinder 24 as well be subsequently described. The needle 16 is not connected directly to needle hub 15 as in the prior art but is removably connected to the washer assembly 28.

The main housing tube 24 is cylindrical in shape for the majority of its length and at the upper end thereof is flared outwardly to form a cone shaped configuration at the top of the tube 24 as shown in FIGS. 1 and 2. The tube or cylinder 24 is made of transparent plastic by means of an injection molding process. The plastic utilized is clear plastic or what is known as "see-through" plastic. Clear or transparent plastic is used to enable the medical technician using the holder 10 to see the entire contents of the inserted syringe 12.

The use of such a transparent plastic allows the medical doctor, nurse or technician to see the scale provided on the syringe 12 and to view the fluid of the syringe and the needle 16 carried by the washer assembly 28. Also, the use of plastic makes the needle protection holder 10 a low cost, disposable item. A suitable plastic is a polycarbonate made by Cyrolite Industries in Azusa, Calif. and which is sold under the trade mark Cyrolite. This plastic, which is commonly used to make medical devices, has been approved for such uses by the United States Food and Drug Administration.

On the inside surface of the cylindrical tube or cylinder 24 at the bottom thereof, there is provided a small lip 32 which protrudes or extends upwardly from the bottom wall 34 of the cylinder 24. The purpose of the lip 32 is to grab and to hold the compression spring 26 onto the bottom wall 34 of the cylinder 24. The lip 32 and bottom wall 34 has an opening 33 through which the needle 16 extends after attachment to the washer assembly 28.

The clear plastic cylinder 24 has generally the same diameter starting at the bottom wall 34 and extending upwardly an appreciable distance and terminating a short distance from the top. As noted in FIG. 1, the cylinder 24 at the upper end thereof flares outwardly to form a cone atop the tubular portion of the cylinder. The cone is designated by the numeral 36 and forms a good resting place for fingers when medical person administers an injection. Cone 36 however is not completely circular in shape as shown in FIGS. 1 and 1A. The cone 36 has a pair of flat surfaces 38 and a pair of curved surfaces 39. The flat surfaces 38 keep the syringe 12 from turning once it is locked in the down position. The flat surfaces 38 also ensure that the thumb pedestal latch 30 grips and holds the syringe 12 properly.

On the inside surface of the main portion of the cylinder 24 are four small elongated guide channels 40. Each guide channel 40 starts just above the bottom lip 32 and extends upwardly following the elongated axis 42 of the cylinder 24. The channels 40 are each closed at the upper end by an end wall 41 and at the lower end by an end wall 43.

Figure 3:
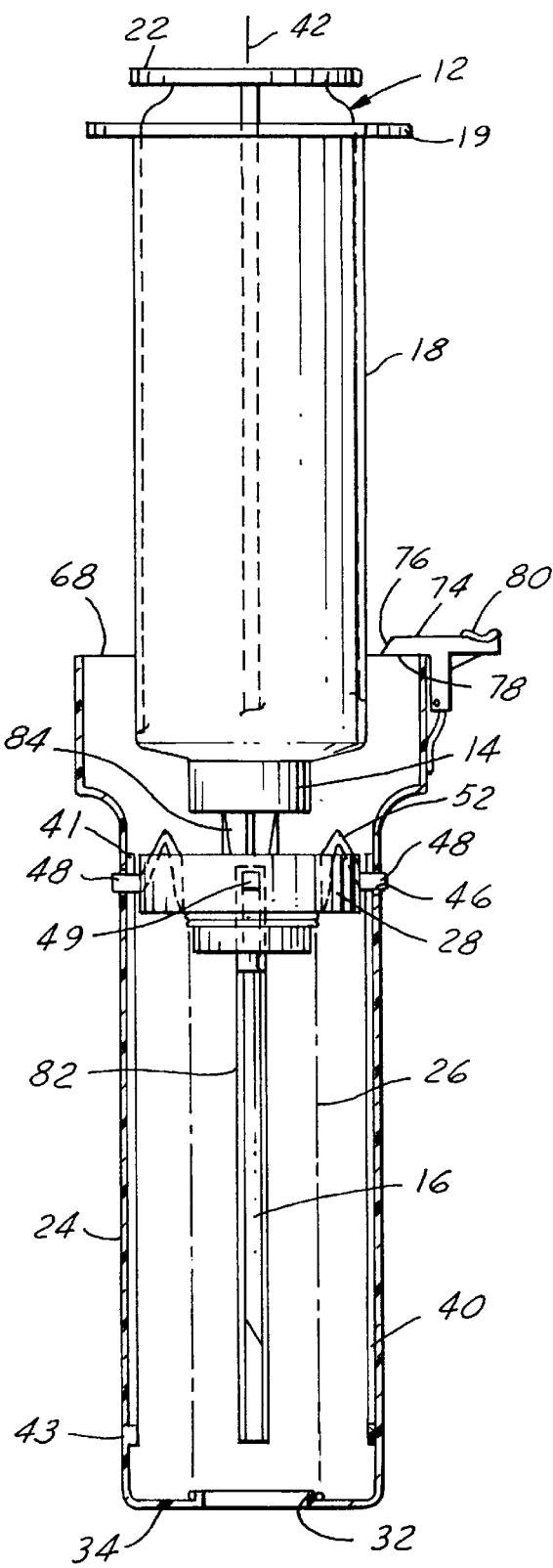
FIG. 3 is a side view of the needle protection holder and syringe with the needle in a locked position within the interior of the holder.
Figure 7:
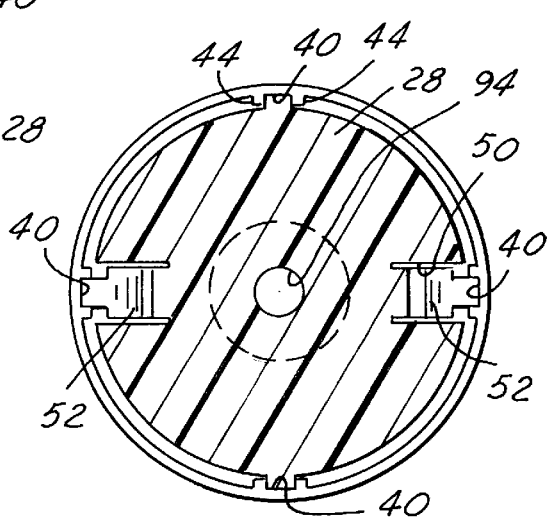
FIG. 7 is a sectional view through the washer, springs and buttons taken on the line 7—7 of FIG. 5.
Figure 8:
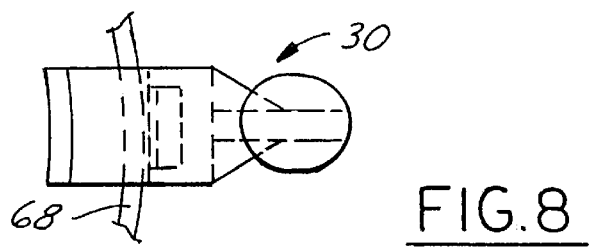
FIG. 8 is a top view of the thumb pedestal latch mounted on the outer surface of the cylinder of the needle protection device.
Figure 10:
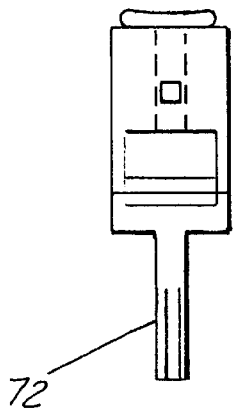
FIG. 10 is a side elevation of the thumb pedestal latch.

Each guide channel 40 is formed by a pair of inwardly extending elongated rails 44 (FIG. 7), the lower ends of which are spaced from the bottom wall 34 as shown in FIG. 3. It should be noted that the rails 44 and therefore the corresponding channels 40 stop at a point where the needle 16 is completely housed within the cylinder 24 as shown in FIG. 3. The rails 44 terminate near the cone formation 36. Each channel 40 has the same length and width as the other channels.

Two of the guide channels 40 are provided at the upper ends thereof with outlet holes 46 which extend through the wall of the main housing tube or cylinder 24 as shown in FIG. 3. The holes 46 are located 180° apart and are provided to receive the lock buttons 48 carried by the attachment washer assembly 28. The other guide channels 40 do not have corresponding openings in the cylinder 24 and receive guide buttons 49 carried by the attachment washer assembly 28.

The purpose of the guide channels 40 is to receive and to track the guide buttons 49 and the lock buttons 48 of the attachment washer or washer assembly 28. The channels 40 and buttons 48 and 49 guide the washer assembly 28 vertically up and down the length of the cylinder 24 without deviating from its intended path or without the washer assembly 28 losing its predetermined orientation. The guide buttons 49 are fixedly carried by the washer assembly 28 and are located 180° apart.

The guide channels 40 also provide a point at which the attachment washer or washer assembly 28 is stopped and locked into position in the cylinder 24 so as not to permit the attachment washer 28 any downward movement. The locking of the attachment washer 28 is created by the two holes 46 provided in the wall of cylinder 24. Such holes 46 are located at the top of the pair of channels 40 as shown in FIG. 3. The attachment washer assembly 28 has a pair of notched out areas or recesses 50 (FIG. 7) in which are located a pair of biasing springs 52. Each spring 52 includes an arm 54, the outer end of which is provided with a lock button 48. During movement of the washer assembly 28 vertically within the main housing tube or cylinder 24, the springs 52 are collapsed inwardly whereby the lock buttons 48 ride in the first pair of channels 40 located 180° apart. The other buttons 49 ride in the second pair of channels located 180° apart. Once the washer assembly 28 reaches the upper end portion of the cylinder 24, as shown in FIG. 3, the biasing springs 52 urge the lock buttons 48 radially outwardly into the openings 46 to lock the washer assembly 28 in place below the enlarged end of the tube 24. It should be noted that although the washer assembly 28 is locked in place, the washer assembly 28 can be unlocked with the proper application of inward forces to the lock buttons 48, when required. From the point at which the guide channels 40 terminate or end their upward extension, the cylinder 24 flares outwardly to form the cone 36 which is located atop the cylinder 24 as shown in the drawings. The cone 36 forms a resting place for fingers when administering an injection to an animal or human being. A finger grip 37 is provided on the exterior surface of the cylinder 24 below the cone 36 and the thumb pedestal latch 30.

Figure 9:
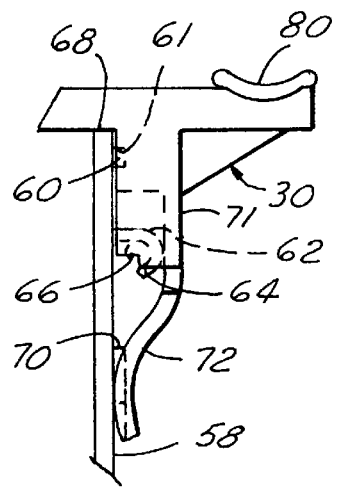
FIG. 9 is a fragmentary view showing the front elevation of the thumb pedestal latch mounted on the outer surface of the cylinder.
Figure 11:
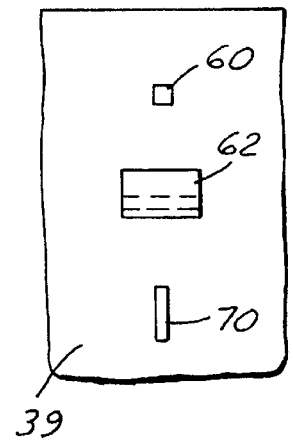
FIG. 11 is a fragmentary side elevation of the upper end of the cylinder and showing the attachment elements on the outer surface of the cylinder for mounting the thumb pedestal latch.

Referring now to FIGS. 1, 1A and 8–11 inclusive, located on the outside surface 58 of the cone 36 between the pair of flat surfaces 38 are three molded items or protuberances which extend outwardly therefrom for mounting the thumb pedestal latch 30. The first molded item is a small square tab 60 which is received in a recess 61 in the body or base 71 of the latch 30 which aids in keeping the thumb pedestal latch 30 from moving side to side when a syringe 12 is locked in place. The second molded item is a half circle shaped downwardly facing protrusion 62 which is set or located at a slight angle as shown in FIG. 9. The protrusion 62 is received in a recess 64 provided in the body 71 of the latch 30 to capture and lock the thumb pedestal latch 30 in place. The recess 64 for the half circle protrusion 62 faces downwardly (FIG. 9) and accepts a tube-like piece 66 molded into the body 71 of the thumb pedestal latch 30. The tube-like piece 66 along with the protrusion 62 permits the thumb pedestal latch 30 to pivot away from the top edge 68 of the cylinder cone 36, thereby permitting the release or unlocking of the syringe 12 inside the main housing tube or cylinder 24 thus enabling the syringe 12 to be retracted. The third and final molded item is a small rectangular shape element 70 that is located behind the spring 72 and helps guide the molded spring 72 of pedestal latch 30 from deviating side-to-side.

The base 71 of the thumb pedestal latch 30 protrudes both towards the inside of the cylinder 24 and away from the outside of the cylinder 24 as illustrated in FIG. 9 where it is attached to the cylinder 24. The thumb pedestal latch 30 has a small lip 74 which has an angled top 76 and a flat bottom 78 (FIG. 3). The angle top 76 allows a syringe to be inserted into the cylinder 24 with a minimum amount of pressure. The flat side or bottom 78 captures the flange 19 of the syringe 12 locking it in place. A thumb pedestal 80 is provided on the body 71 outboard or outside of the cone 36. When pressure is applied to the thumb pedestal 80, the flexible spring 72 on its underside allows the thumb pedestal 80 to move outwardly and downwardly away from the flange 19 of the syringe 12. This results in the release of the syringe 12 from its locked position.

The compression spring 26, upon release of the syringe 12, pushes the syringe 12, washer assembly 28 and needle 16 upwardly the length of the slotted guide channels 40. The openings 46 in the pair of channels 40 as viewed in FIG. 3 capture the lock buttons 48 of the attachment washer assembly 28 thereby locking the assembly 28 with the cylinder 24. Since the needle 16 and the syringe 12 are connected to the attachment washer assembly 28, they are also locked inside the cylinder 24 for safe keeping. At this point, the original safety cap for the needle can be reapplied without fear of receiving a needle prick or the entire assembly 10 with syringe 12 can be discarded or disposed of safely.

The compression spring 26 fits into the main housing unit as best illustrated in FIG. 3. Its diameter and length depends on the size of the needle protection assembly 10 being used. Different size devices can be produced to accommodate the syringes which are currently available on the market for serving humans as well as animals. The only requirement of the spring 26 is to have enough strength to pull a needle from a body (human or animal) and to retract or return the spring to a position inside the cylinder 24. Such compression springs 26 are common and in every day use in many types of devices.

The attachment washer assembly 28 is of circular configuration like a washer and is provided on its outer edges with two pairs of radially extending buttons. Two buttons 49 are stationary while the other two buttons 48 are located at the ends of the spring arms 54 of the self-contained springs 52. Viewing the washer from the top, the buttons in each pair are located 180° apart. The small buttons 49 fit perfectly into the pair of slotted guide channels 40 located on the inside of the cylinder 24. The pair of spring loaded buttons 48 and holes 46 are the means by which the washer assembly 28 locks itself in the cylinder 24 after the needle protection holder 10 has been used and the needle 16 entrained in the cylinder 24. The spring loaded buttons 48 project themselves into the holes 46 as best illustrated in FIG. 3. The two plastic tension springs 52 which are molded into the washer at the time of manufacture, causes the buttons 48 to project themselves into the openings 46. The buttons 48 and 49 are also placed on and secured to the plastic washer during manufacture of the washer assembly 28.

Figure 4:
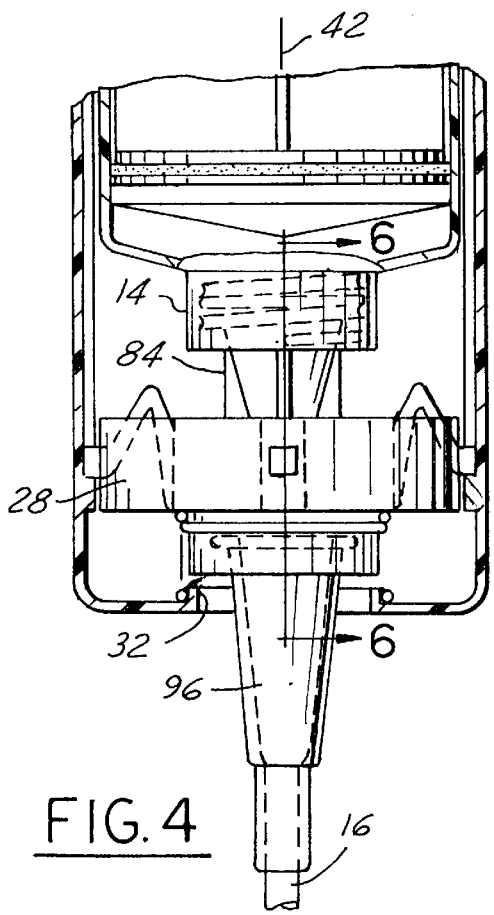
FIG. 4 is a fragmentary side elevation of the needle protection holder and a Luer Lok syringe.
Figure 5:
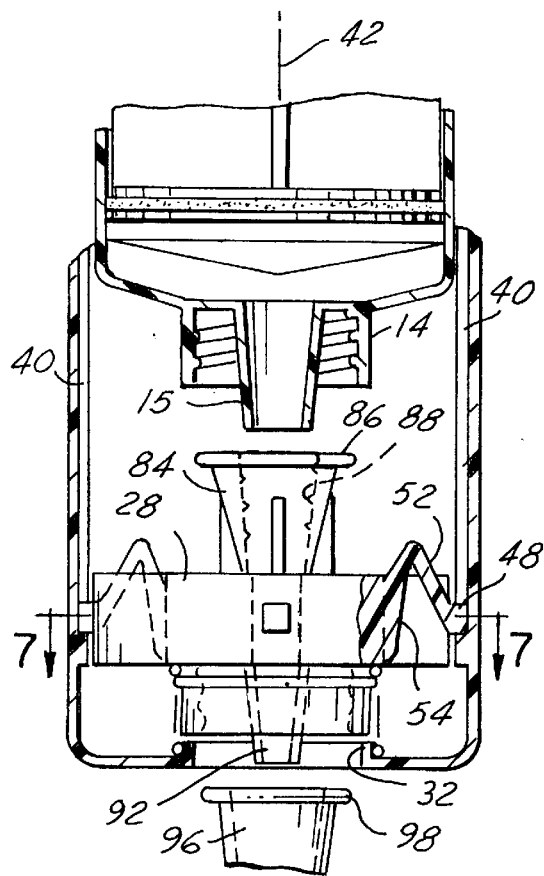
FIG. 5 is a fragmentary side elevation of the needle protection holder and syringe showing how a syringe fits onto the needle receiving cup of the attachment washer assembly and a needle fits onto the Luer Lok threaded cup of the assembly which is carried within the main tube or housing of the holder.
Figure 6:
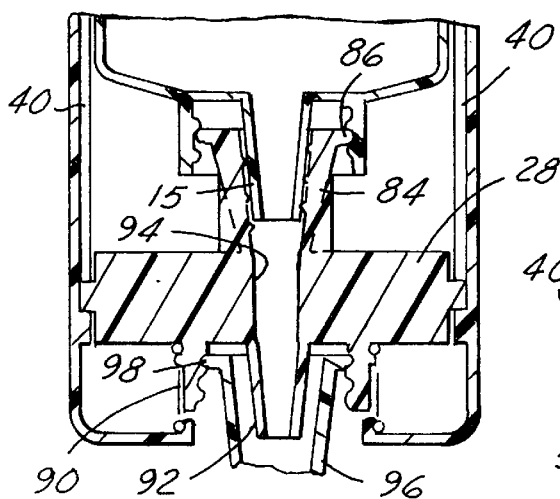
FIG. 6 is a fragmentary cross sectional view taken on the line 6—6 of FIG. 4.

Located at the top of the washer assembly 28 is a cup 84 (FIGS. 4–6). Cup 84 is of the same size and shape as a cup on a Lure Lok needle. The cup 84 on the top edge thereof is provided with a lip 86 that protrudes outwardly. This lip or edge 86 provides a means by which the cup 84 attaches itself to a Lure Lok syringe 12 as previously described. The lip 86 acts the same way as a screw and nut go together utilizing threads. On the inside of the cup 84 is a small shaped thread 88 extending around its circumference. Thread 88 is rounded on its top side and is flat on its underside. The sharp thread 88 cuts or bits into a regular point syringe or into needle hub 15, ensuring a secured fit with the cup 84 during the retraction process. On the bottom of the washer assembly 28 is provided the other half of the Luer Lok. This is the same locking mechanism found on the bottom of a Luer Lok syringe and is used to secure a Lure Lok needle in place. The locking mechanism includes a Luer Lok coupling 90 and a needle hub 92. The washer 28 has an axially extending passage 94 which is in fluid communication with the interior of the syringe 12 via the openings in the cup 84, needle hub 15 and the needle 16. The needle 16 is provided with an internally threaded cup 96 having a flange 98 which locks in the Luer Lok coupling 96 as is well known in the art. The passage or hole 94 allows for the passage of fluid from the syringe 12 to the needle 16 or from the patient's body via the needle 16 to the syringe 12 such as when withdrawing blood from an animal or from a human person.

The washer assembly 28 including the biasing springs, buttons and cup components are made from plastic material such as polypropolene, nylon or other suitable plastic materials.

On the outside surface 39 of the latch mechanism 30 is a small rounded lip 74. The purpose of the lip 74 is to capture the syringe flange 19 and thereby hold the compression spring 26 in place. With the Luer Lok needle cup 84 mounted on the top side of the washer assembly 28 and the threaded Luer Lok coupling 90 mounted on the bottom of the washer, technicians will find it easy to connect the needle 16 via the cup 96 to the Luer Lok coupling 90 of the washer assembly 28. It is no more difficult then it would be to connect the needle and syringe together without the use of the needle protection assembly 10.

The thumb pedestal latch 30 is made from clear plastic material utilizing an injection molding process. The thumb pedestal latch 30 has four main characters or components including a body or base 71, the thumb pedestal 80, the lip 74 and the tension spring 72. The base 71 is rectangular in shape with a tube 66 running horizontally through its middle. It is the same width as a half circle shaped tab 62 found on the outside surface of the cone 36. The tube 66 fits perfectly into the half circle shaped tab 62 on the cylinder 24 and is the means for locking the two parts together.

Located above the tube 66 is a square slot or recess 61 that runs vertically. This slot 61 is slightly wider than the square protrusion 60 on the cylinder surface 39. Its purpose is to keep the thumb pedestal latch 30 from moving side to side once it has been mounted in place. The top of the thumb pedestal latch branches off into two different directions. To the outside of the unit lies the thumb pedestal 80. It has a narrow V-shaped shaft with a concave oval platform at its tip. This is where a persons's thumb would rest and apply pressure to activate the latch 30. The concave platform or pedestal 80 has a cross pattern of raised ridges on it. The ridges ensure a minimal amount of slippage when pressure is applied. To the inside of the unit, that is, the part facing the inside of the cone 36 of the cylinder 24, is the angled lip 74. It is flat on the bottom side 78 and protrudes into the cone 36, when mounted, just far enough to grab and hold onto the flange 19 of the syringe 12. The top side of lip 74 is angled at 76 to allow a syringe passage with a minimal amount of downward pressure. Once the thumb pedestal latch 30 grabs onto the syringe 12, it is held in position by means of a tension spring 72. The tension spring 72 is located just below the base. It is a curved shaped piece of plastic that has also been molded into the thumb pedestal unit 30. The spring 72 produces pressure against the main body of the cone 36 and has two very small finger-like protrusions 73 that fit over a rectangular shaped item 70 on the cylinder 24. The fingers 73 keep the spring 72 from deviating side-to-side and ensure that proper tracking occurs.

With such a construction, medical technicians can use the needle protection holder 10 with one hand allowing them the freedom to perform other tasks with their other hands.

The needle protection holder 10 of the present invention is designed to protect medical personnel from exposure to infectious diseases. It is a simple and unique product whose value, when compared with its relative expense, would be recognized or appreciated by any risk management program. It is designed to accept more than one type of syringe. Further, the needle protection holder 10, with small changes, can be adapted to fit every standard manufactured syringe used for humans and for animals. In use, once a needle is placed into the body of patient or of an animal using the needle protection holder 10, the needle will never contact the open air, another patient or the technician unless the technical takes a direct action to unlock the device by depressing the lock buttons 48 inwardly and to disengage the buttons 48 from the holes 46. Thereafter, the device could be reused. Earlier devices which have claimed to isolate the needle after use have drawbacks or restrictions. Some devices require you to use all of the contents of the syringe before it retracts the needle into the provided shield. Some have clumsy release latches of awkward designs. Still others are made to be used only with the manufacturers syringes which limits the ability of the hospital or clinic to choose to purchase the type of syringe which best suits their purpose and budget. The needle protection holder 10 of the present invention provides choices for the medical technicians. Medical personnel can choose what syringe to use with the present invention; when to retract the needle; and whether or not the needle protection holder is to be used again. The holder design of the present invention permits it to be used in the same manner as a Luer Lok syringe would normally be used, with the additional ability to protect all medical personnel from common, deadly needle sticks or punctures.

It is to be understood that the embodiment of the invention herein shown and described is to be taken as a preferred example of the same, and that various changes in size, shape and arrangement of parts may be resorted to without departing from the spirit of the invention or the scope of the claims which follow. Further, while the principals of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principals.

What I claim is:

1. A needle protection holder to be interposed between a hypodermic syringe and a needle, said holder comprising:

a cylinder having a longitudinal axis;

said cylinder being open at one end and having a bottom wall at the other end;

a washer of generally cylindrical configuration telescopically movable in said cylinder along said longitudinal axis;

said washer having first and second sides and a cylindrical wall;

a centrally located passage in said washer between said first and second sides;

first coupling means fixed to one side of said washer for attachment to the hypodermic syringe;

second coupling means fixed to the second side of said washer for attachment to the needle;

guide means interposed between said cylinder and said washer for maintaining the orientation of said washer in said cylinder;

spring means interposed in said cylinder between said bottom wall of said cylinder and said second side of said washer for biasing said washer and the needle carried thereby towards the open end of said cylinder; and latch means carried by the upper end of said cylinder for engagement with the syringe to retain the syringe within said holder.

2. The needle protection holder defined in claim 1 wherein the upper end of said cylinder is enlarged to provide an entrance for the hypodermic syringe and a mounting place for said latch means.

3. The needle protection holder defined in claim 2 wherein said latch means is in the form of a thumb pedestal latch which is pivotably mounted on the exterior surface of said enlarge upper end of the cylinder.

4. The needle protection holder defined in claim 1 wherein said guide means includes four elongated channels located 90° apart on the inner surface of said cylinder and four outwardly extending buttons located 90° apart and mounted on the cylindrical wall of said washer, one button for each channel, said buttons rideable in said channels for maintaining the orientation of said washer in said cylinder.

5. The needle protection holder defined in claim 4 wherein a first pair of said channels at the upper ends thereof are provided with button openings in the wall of the cylinder which are located 180° apart, the buttons corresponding to said first pair of channels being resiliently carried by said washer and urged into said button openings when said washer overlies said button openings to hold and thereby fix said washer and the needle carried thereby in said cylinder.

6. The needle protection holder defined in claim 1 wherein said first coupling means is a Luer Lok type coupling with an internally threaded passage therethrough which is aligned with said centrally located passage in said washer.

7. The needle protection holder defined in claim 6 wherein said second coupling means is a Luer Lok type coupling with an internally threaded passage therethrough which is aligned with the centrally located passage in said washer.

8. The needle protection holder defined in claim 1 wherein said washer has a pair of recesses in said cylindrical wall between said first and second sides located 180° apart, and a pair of biasing springs located in said recesses and carried by said washer, said biasing springs including arms, the outer ends of said arms being provided with buttons which form part of said guide means.

9. The needle protection holder as defined in claim 8 wherein said washer, biasing springs and buttons are made from a plastic material.

10. The needle protection holder as defined in claim 9 wherein said plastic material is taken from the group of plastics including polypropolene and nylon.

11. The needle protection holder as defined in claim 1 wherein said cylinder is made from a clear plastic material which permits viewing of the syringe.

12. A needle protection holder to be interposed between a hypodermic syringe and a needle, said holder comprising:

a cylinder having a longitudinal axis;

said cylinder being open at one end and having a bottom wall at the other end;

a washer of generally cylindrical configuration telescopically movable in said cylinder along said longitudinal axis;

said washer having first and second sides and a cylindrical wall;

a centrally located passage in said washer between said first and second sides;

first coupling means fixed to one side of said washer for attachment to the hypodermic syringe;

second coupling means fixed to the second side of said washer for attachment to the needle;

said cylinder being made from a clear plastic material and having inner and outer surfaces;

said inner surface having thereon four elongated channels which are equally spaced apart;

the cylindrical wall of said washer being provided with four buttons which are equally spaced apart and are received in said channels, one button for each channel, said buttons maintaining the orientation of said washer in said cylinder;

spring means interposed in said cylinder between said bottom wall of said cylinder and said second side of said washer for biasing said washer and the needle carried thereby towards the open end of said cylinder; and latch means carried by the upper end of said cylinder for engagement with the syringe to retain the syringe within said holder.

13. The needle protection holder defined in claim 12 wherein the upper end of said cylinder is enlarged to provide an entrance for the hypodermic syringe and a mounting place for said latch means.

14. The needle protection holder defined in claim 13 wherein said latch means is in the form of a thumb pedestal latch which is pivotably mounted on the exterior surface of said enlarge upper end of the cylinder.

15. The needle protection holder defined in claim 12 wherein a first pair of said channels at the upper ends thereof are provided with button openings in the wall of the cylinder which are located 180° apart, the buttons corresponding to said first pair of channels being resiliently carried by said washer and urged into said button openings when said washer overlies said button openings to hold and thereby fix said washer and the needle carried thereby in said cylinder.

16. The needle protection holder defined in claim 12 wherein said first coupling means is a Luer Lok type coupling with an internally threaded passage therethrough which is aligned with said centrally located passage in said washer.

17. The needle protection holder defined in claim 16 wherein said second coupling means is a Luer Lok type coupling with an internally threaded passage therethrough which is aligned with the centrally located passage in said washer.

18. The needle protection holder defined in claim 12 wherein said washer has a pair of recesses in said cylindrical wall between said first and second sides located 180° apart, and a pair of biasing springs located in said recesses and carried by said washer, said biasing springs including arms, the outer ends of said arms being provided with buttons which form part of said guide means.

19. The needle protection holder as defined in claim 18 wherein said washer, biasing springs and buttons are made from a plastic material.

20. The needle protection holder as defined in claim 19 wherein said plastic material is taken from the group of plastics including polypropolene and nylon.

21. The needle protection holder as defined in claim 12 wherein said cylinder is made from a clear plastic material which permits viewing of the syringe.

22. The combination of a hypodermic syringe, needle and a needle protection holder as defined in claim 1.

* * * * *